(12) United States Patent
Hathaway et al.

(10) Patent No.: US 7,988,669 B2
(45) Date of Patent: Aug. 2, 2011

(54) PORT FIXATION WITH FILAMENT ACTUATING MEMBER

(75) Inventors: Peter Hathaway, Lebanon, CT (US); Gregory Fischvogt, Hamden, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/641,906

(22) Filed: Dec. 18, 2009

(65) Prior Publication Data

US 2010/0211012 A1 Aug. 19, 2010

Related U.S. Application Data

(60) Provisional application No. 61/153,078, filed on Feb. 17, 2009.

(51) Int. Cl.
*A61M 5/178* (2006.01)
(52) U.S. Cl. ................................. 604/164.01
(58) Field of Classification Search ............ 604/164.01, 604/164.04, 174; 600/204; 606/185, 191
See application file for complete search history.

(56) References Cited

U.S. PATENT DOCUMENTS

| | | | |
|---|---|---|---|
| 3,509,883 A | 5/1970 | Dibelius |
| 3,789,852 A | 2/1974 | Kim et al. |
| 4,018,230 A | 4/1977 | Ochiai et al. |
| 4,141,364 A | 2/1979 | Schultze |
| 4,411,655 A | 10/1983 | Schreck |
| 4,650,466 A | 3/1987 | Luther |
| 4,921,479 A | 5/1990 | Grayzel |
| 4,954,126 A | 9/1990 | Wallstén |
| 5,002,557 A | 3/1991 | Hasson |
| 5,041,093 A | 8/1991 | Chu |
| 5,122,122 A | 6/1992 | Allgood |
| 5,147,316 A | 9/1992 | Castillenti |
| 5,158,545 A | 10/1992 | Trudell et al. |
| 5,176,697 A | 1/1993 | Hasson et al. |
| 5,183,464 A | 2/1993 | Dubrul et al. |
| 5,197,971 A | 3/1993 | Bonutti |
| 5,201,756 A | 4/1993 | Horzewski et al. |
| 5,203,773 A | 4/1993 | Green |
| 5,217,451 A | 6/1993 | Freitas |
| 5,232,451 A | 8/1993 | Freitas et al. |
| 5,234,455 A | 8/1993 | Mulhollan |
| 5,248,302 A | 9/1993 | Patrick et al. |
| 5,273,529 A | 12/1993 | Idowu |
| 5,279,564 A | 1/1994 | Taylor |
| 5,279,575 A | 1/1994 | Sugarbaker |
| 5,290,249 A | 3/1994 | Foster et al. |
| 5,312,417 A | 5/1994 | Wilk |
| 5,318,012 A | 6/1994 | Wilk |
| 5,318,588 A | 6/1994 | Horzewski et al. |
| 5,320,611 A | 6/1994 | Bonutti et al. |
| 5,387,196 A | 2/1995 | Green et al. |
| 5,407,430 A | 4/1995 | Peters |
| 5,431,676 A | 7/1995 | Dubrul et al. |
| 5,443,484 A | 8/1995 | Kirsch et al. |

(Continued)

*Primary Examiner* — Nicholas D Lucchesi
*Assistant Examiner* — Aarti B Berdichevsky (57) ABSTRACT

The present disclosure relates to surgical access apparatus for positioning within a percutaneous tissue tract to facilitate access to an underlying surgical worksite. In one embodiment, the disclosed surgical access includes a housing with proximal and distal ends that is configured to removably receive at least one surgical instrument, a tubular member that extends distally from the housing along a longitudinal axis, a connective member that is secured to the tubular member, either internally or externally, at least one filament that is secured to the connective member so as to extend proximally therefrom, and at least one manual member that is secured to the at least one filament.

15 Claims, 6 Drawing Sheets

U.S. PATENT DOCUMENTS

| | | |
|---|---|---|
| 5,454,365 A | 10/1995 | Bonutti |
| 5,460,170 A | 10/1995 | Hammerslag |
| 5,512,053 A | 4/1996 | Pearson et al. |
| 5,540,658 A | 7/1996 | Evans et al. |
| 5,549,595 A | 8/1996 | Freitas |
| 5,549,627 A | 8/1996 | Kieturakis |
| 5,618,309 A | 4/1997 | Green et al. |
| 5,637,097 A | 6/1997 | Yoon |
| 5,674,240 A | 10/1997 | Bonutti et al. |
| 5,685,826 A | 11/1997 | Bonutti et al. |
| 5,707,362 A | 1/1998 | Yoon |
| 5,713,870 A | 2/1998 | Yoon |
| 5,730,725 A * | 3/1998 | Yoon ................. 604/101.05 |
| 5,766,220 A | 6/1998 | Moenning |
| 5,782,813 A | 7/1998 | Yoon |
| 5,814,058 A | 9/1998 | Carlson et al. |
| 5,817,062 A | 10/1998 | Flom et al. |
| 5,820,600 A * | 10/1998 | Carlson et al. ........... 604/167.03 |
| 5,827,319 A | 10/1998 | Carlson et al. |
| 5,836,913 A | 11/1998 | Orth et al. |
| 5,857,999 A | 1/1999 | Quick et al. |
| 5,882,340 A | 3/1999 | Yoon |
| 5,888,196 A | 3/1999 | Bonutti |
| 5,935,107 A | 8/1999 | Taylor et al. |
| 5,941,898 A | 8/1999 | Moenning et al. |
| 5,944,691 A | 8/1999 | Querns et al. |
| 5,951,588 A | 9/1999 | Moenning |
| 5,961,499 A | 10/1999 | Bonutti et al. |
| 6,059,816 A | 5/2000 | Moenning |
| 6,080,174 A | 6/2000 | Dubrul et al. |
| 6,187,000 B1 | 2/2001 | Davison et al. |
| 6,210,370 B1 | 4/2001 | Chi-Sing et al. |
| 6,245,052 B1 | 6/2001 | Orth et al. |
| 6,293,909 B1 | 9/2001 | Chu et al. |
| 6,325,812 B1 | 12/2001 | Dubrul et al. |
| 6,338,730 B1 | 1/2002 | Bonutti et al. |
| 6,387,095 B1 | 5/2002 | Kennett et al. |
| 6,450,989 B2 | 9/2002 | Dubrul et al. |
| 6,451,041 B1 | 9/2002 | Moenning et al. |
| 6,461,346 B1 * | 10/2002 | Buelna .................. 604/500 |
| 6,494,893 B2 | 12/2002 | Dubrul et al. |
| 6,589,225 B2 | 7/2003 | Orth et al. |
| 6,613,038 B2 | 9/2003 | Bonutti et al. |
| 6,620,129 B2 | 9/2003 | Stecker et al. |
| 6,632,197 B2 | 10/2003 | Lyon |
| 6,692,462 B2 | 2/2004 | Mackenzie et al. |
| 6,702,787 B2 * | 3/2004 | Racenet et al. ................ 604/256 |
| 2002/0035373 A1 | 3/2002 | Carlson et al. |
| 2003/0216770 A1 | 11/2003 | Persidsky et al. |

* cited by examiner

PORT FIXATION WITH FILAMENT ACTUATING MEMBER

CROSS REFERENCE TO RELATED APPLICATION

The present application claims the benefit of and priority to U.S. Provisional Application Ser. No. 61/153,078 filed on Feb. 17, 2009, the entire contents of which are incorporated herein by reference.

BACKGROUND

1. Technical Field

The present disclosure relates to surgical access apparatus for positioning within an opening formed in a patient's tissue. More particularly, the present disclosure relates to surgical access apparatus that are repositionable to facilitate anchoring within a percutaneous opening, and capable of removably receiving one or more surgical instruments.

2. Background of the Related Art

In contemporary medical practice, many surgical procedures are performed through small incisions formed in the skin, as compared to the larger incisions typically required in traditional procedures, in an effort to reduce both patient trauma and recovery time. Generally, such procedures are referred to as "endoscopic," unless performed in the patient's abdomen, in which case the procedure is referred to as "laparoscopic," or on a joint, ligament, or the like, in which case the procedure is referred to as "arthroscopic."

Throughout the present disclosure, "endoscopic," "laparoscopic," and "arthroscopic" procedures may be collectively referred to as "minimally invasive" procedures.

Typically, a minimally invasive surgical procedure will include the use of a surgical access apparatus or portal member to facilitate entry into a surgical worksite positioned beneath the patient's tissue with surgical instrumentation, e.g., endoscopes, obturators, staplers, and the like. A typical surgical access apparatus defines a passageway or lumen through which the surgical instrumentation is inserted and the procedure is carried out.

While many varieties of surgical access apparatus are known in the art, a continuing need exists for a surgical access apparatus that may be releasably and reliably secured within the patient's tissue throughout the course of a minimally invasive procedure.

SUMMARY

In one aspect of the present disclosure, a surgical access apparatus is disclosed for positioning within a percutaneous tissue tract to facilitate access to an underlying surgical worksite. The disclosed surgical access apparatus includes a housing with proximal and distal ends that is configured to removably receive at least one surgical instrument, a tubular member that extends distally from the housing along a longitudinal axis, a connective member that is secured to the tubular member, either internally or externally, at least one filament that is secured to the connective member so as to extend proximally therefrom, and, optionally, at least one manual member that is secured to the at least one filament.

The tubular member defines an axial lumen that is configured and dimensioned to allow the at least one surgical instrument to pass therethrough. The lumen of the tubular member includes an internal dimension that is smaller than an outer dimension of the at least one surgical instrument.

The tubular member is repositionable between a first position, in which the tubular member is configured for at least partial insertion into the tissue tract, and a second position, in which the tubular member is configured to facilitate anchoring of the tubular member within the tissue tract. In the first position, the tubular member includes a first outer dimension, and in the second position, the tubular member defines a tissue engaging portion with a second outer dimension that is larger than the first outer dimension.

The tubular member includes a plurality of fibers that are braided together to define a mesh adapted for radial expansion to allow for insertion of the surgical instrument into the lumen of the tubular member. In one embodiment of the surgical access apparatus, the fibers include a substantially elastic material such that the tubular member maintains a substantially constant axial dimension upon radially expansion. Alternatively, however, the fibers may include a substantially inelastic material such that the tubular member experiences a measure of axial shortening upon radial expansion.

The at least one manual member is configured and dimensioned for grasping by a clinician such that the at least one filament is movable in a proximal direction to facilitate selective repositioning of the tubular member from the first position to the second position.

The surgical access apparatus may further include a membrane that is disposed about at least a portion of the elongate member to facilitate anchoring of the elongate member within the tissue tract.

Additionally, or alternatively, the housing of the surgical access apparatus may include locking structure that is configured to engage one or more of the at least one filament and the at least one manual member to thereby maintain the second position of the tubular member. It is envisioned that the locking structure may include at least one channel formed in the housing that is configured to at least partially receive the at least one filament. The locking structure may further include a locking member adapted for repositioning between unlocked and locked positions and defining a channel therethrough that is configured to at least partially receive the at least one filament. In this embodiment, when the locking member is in the unlocked position, the channel of the locking member and the channel formed in the housing are substantially aligned, and when the locking member is in the locked position, the channel of the locking member and the channel formed in the housing are substantially misaligned. The present disclosure contemplates that the locking member may be biased towards the locked position by a biasing member.

In another aspect of the present disclosure, a method of percutaneously accessing a surgical worksite positioned beneath a patient's tissue is disclosed. The method includes the steps of (i) providing a surgical access apparatus including a housing with proximal and distal ends that is configured to removably receive at least one surgical instrument, a tubular member that extends distally from the housing, a connective member that is secured to the tubular member, at least one filament that is secured to the connective member so as to extend proximally therefrom, and at least one manual member that is secured to the at least one filament; (ii) advancing the tubular member distally into an opening in the tissue while in the first position; and (iii) repositioning the tubular member from the first position to the second position to anchor the surgical access apparatus within the tissue.

The tubular member is adapted to removably receive the at least one surgical instrument, and is repositionable between a first position, in which the tubular member is configured for at least partial insertion into the opening in the tissue, and a second position, in which the tubular member is configured to facilitate anchoring of the tubular member within the tissue.

The at least one manual member is configured and dimensioned for grasping by a clinician such that the at least one filament is movable in a proximal direction to cause corresponding movement of the connective member to thereby facilitate selective repositioning of the tubular member from the first position to the second position.

The step of providing a surgical access apparatus may include providing a surgical access apparatus wherein the lumen of the tubular member includes an internal dimension that is smaller than an outer dimension of the at least one surgical instrument to minimize tissue trauma upon insertion of the tubular member into the percutaneous opening.

It is also envisioned that the provided surgical access apparatus may incorporate a tubular member that includes a mesh of braided fibers allowing for radial expansion of the tubular member to facilitate insertion of the surgical instrument into the lumen thereof In one embodiment of the disclosed method, the housing may include locking structure that is configured to engage one or more of the at least one filament and the at least one manual member for maintaining the second position of the tubular member. In this embodiment, the disclosed method may further include the step of attaching one or more of the at least one filament and the at least one manual member to the locking structure to maintain the second position of the tubular member.

It is also contemplated that the disclosed method may also include the step of positioning the at least one surgical instrument within the surgical access apparatus to percutaneously access the surgical worksite.

These and other features of the surgical access apparatus disclosed herein will become more readily apparent to those skilled in the art through reference to the detailed description of various embodiments of the present disclosure that follows.

BRIEF DESCRIPTION OF THE DRAWINGS

Various embodiments of the present disclosure are described herein below with references to the drawings, wherein.

DETAILED DESCRIPTION OF THE EMBODIMENTS

In the drawings, and in the following description, like references numerals will identify similar or identical elements. Throughout the following description, the term "proximal" will refer to the end of the presently disclosed surgical access apparatus, or component thereof, that is closest to the clinician during proper use, while the term "distal" will refer to the end that is furthest from the clinician. Additionally, the term "tissue tract" should be understood as referring to any opening in a patient's tissue, whether formed by the clinician or pre-existing.

Figure 1:
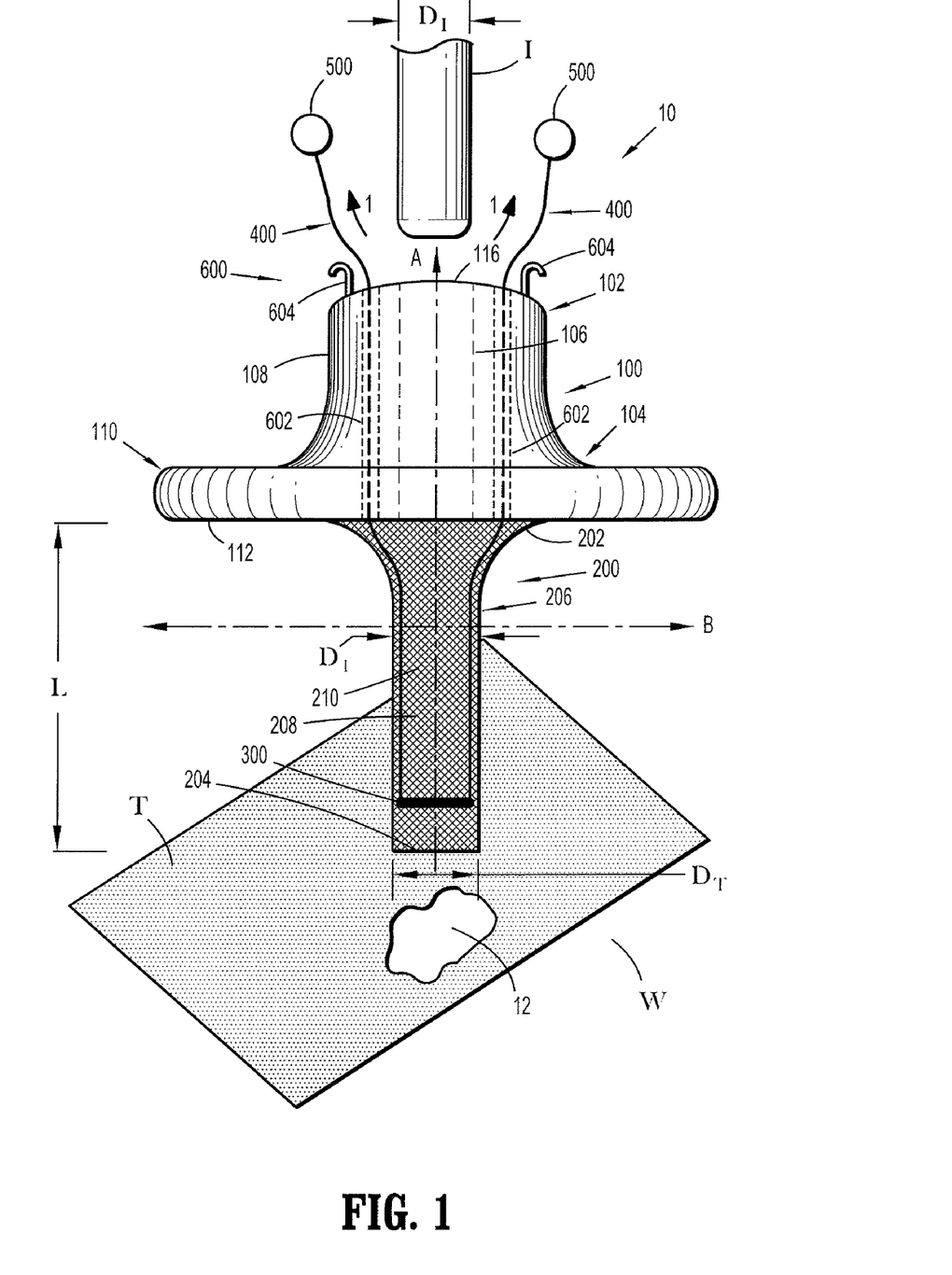
FIG. 1 is a side, schematic view of a surgical access apparatus including a housing and a tubular member in accordance with one embodiment of the present disclosure, wherein the tubular member is shown in a first position.
Figure 2:
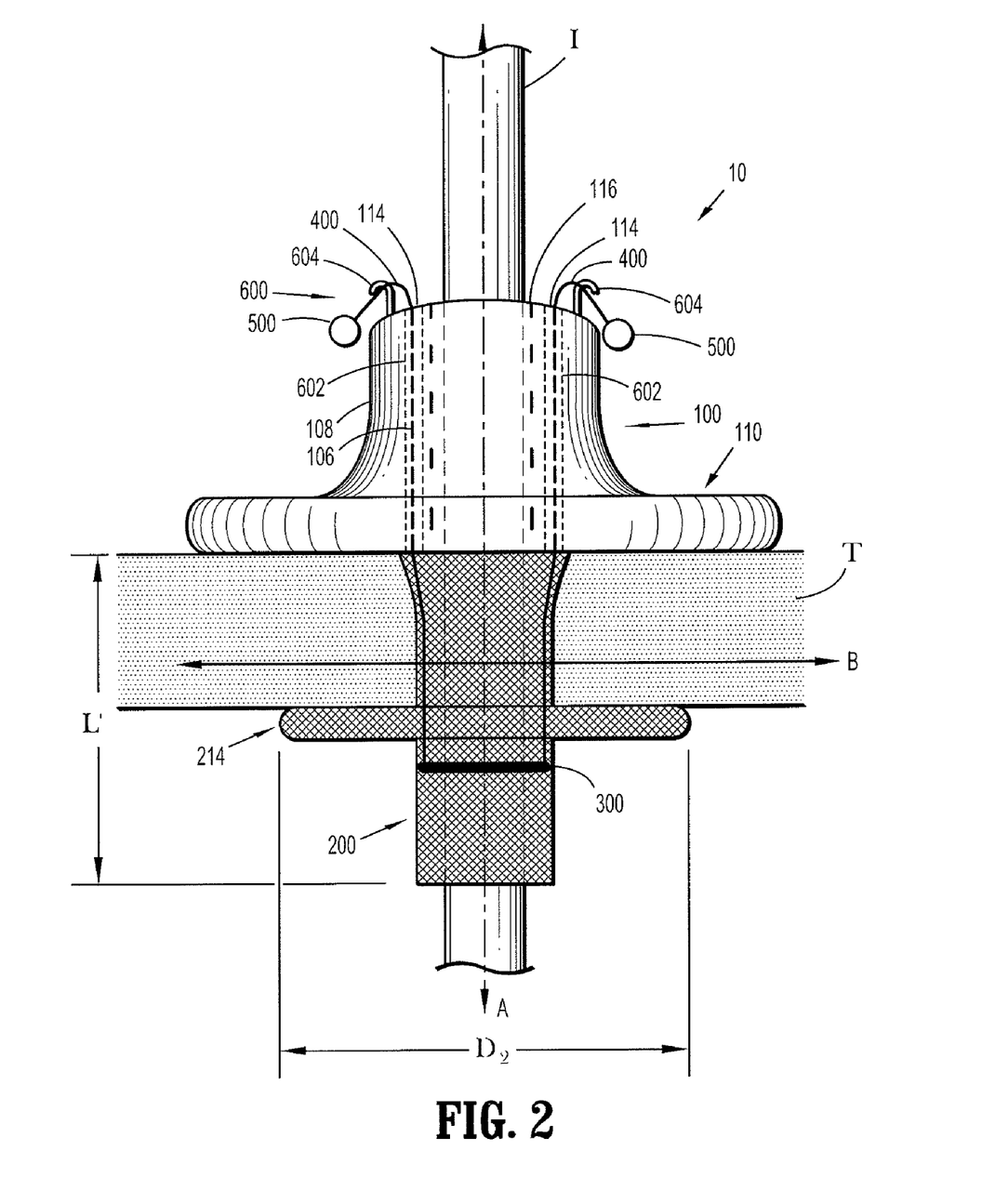
FIG. 2 is a side, schematic view of the surgical access apparatus shown in FIG. 1 illustrating the tubular member in a second position within a tissue tract formed in a patient's tissue.

With reference to FIGS. 1 and 2, a surgical access apparatus 10 is disclosed that is removably positionable within a tissue tract or opening 12 formed in a patient's tissue "T." The surgical access apparatus 10 is employable during the course of a surgical procedure, e.g., a minimally invasive procedure, to facilitate access to a surgical worksite "W," such as a patient's underlying cavities, tissues, organs, or the like, with one or more surgical instruments "I." In one aspect of the present disclosure, the surgical access apparatus 10 includes a housing 100, a tubular member 200, a connective member 300, one or more filaments 400, and at least one manual member 500.

The housing 100 includes respective proximal and distal ends 102, 104, and may be fabricated from any suitable biocompatible material including moldable polymeric materials, stainless steel, titanium, or the like. The housing 100 is configured for manual engagement by a clinician and includes an opening 106 extending therethrough that is configured for the reception and passage of the surgical instrument "I," which defines an outer transverse dimension "$D_1$." The housing 100 includes an outer wall 108 defining a flange 110 with a distal surface 112, and may optionally include an internal seal or valve (not shown), such as a duck-bill or zero-closure valve, that is adapted to close in the absence of the surgical instrument "I". Examples of suitable internal seals or valves are discussed in commonly assigned U.S. Pat. Nos. 5,820,600 to Carlson, et al. and 6,702,787 to Racenet et al., which issued on Oct. 13, 1998 and Mar. 9, 2004, respectively, the entire contents of which are incorporated by reference herein. The housing 100 further includes locking structure 600, which will be discussed in detail below.

The tubular member 200 extends distally from the housing 100 along a longitudinal axis "A" a length "L," and includes a proximal end 202 and a distal end 204. The tubular member 200 is configured as a braid 206 formed by a mesh of biocompatible fibers 208, and defines an axial lumen 210 therethrough that is configured for the reception and passage of the surgical instrument "I". Specifically, the lumen 210 of the tubular member 200 defines an internal transverse dimension "$D_T$" that is less than the outer transverse dimension "$D_1$" of the surgical instrument "I." Consequently, insertion of the surgical instrument "I" into the lumen 210 of the tubular member 200 will cause the tubular member 200 to expand outwardly along an axis "B" that is transverse, e.g., orthogonal, in relation to the longitudinal axis "A." In one embodiment of the tubular member 200, the fibers 208 may be formed from a substantially elastic material, which allows the length "L" of the tubular member 200 to remain substantially constant during outward expansion. However, in an alternative embodiment, the fibers 208 comprising the braid 206 may be formed from a substantially inelastic material, e.g., polyamide fiber, stainless steel, or the like, such that tubular member 200 experiences a measure of shortening along the longitudinal axis "A" upon the introduction of surgical instrument "I", further details of which may be obtained through reference to U.S. Pat. No. 5,431,676 to Dubrul et al., the entire contents of which are incorporated by reference herein. The fibers 208 comprising the braid 206 may be of any suitable configuration, including but not limited to round, flat, ribbon-like, or square.

With continued reference to FIGS. 1 and 2, the connective member 300 will be discussed. The connective member 300 may be formed from any suitable biocompatible material, including but not limited to polymeric materials or rubber. Desirably, the connective member 300 is formed from a resilient, substantially non-rigid material such that the connective member 300 is capable of deformation, e.g., compression, to facilitate insertion of the tubular member 200 into the tissue tract 12. In one specific embodiment of the present disclosure, the connective member 300 is formed from an expandable material such that the connective member 300 is deformed radially as the surgical instrument "I" is passed therethrough. In this embodiment, the connective member 300 forms a substantially fluid-tight seal with the surgical instrument "I" to inhibit the escape of fluid, e.g., insufflation gas in the case of a laparoscopic surgical procedure or an irrigant solution in the case of an arthroscopic surgical procedure, from the surgical worksite "W" about the tubular member 200.

Figure 3:
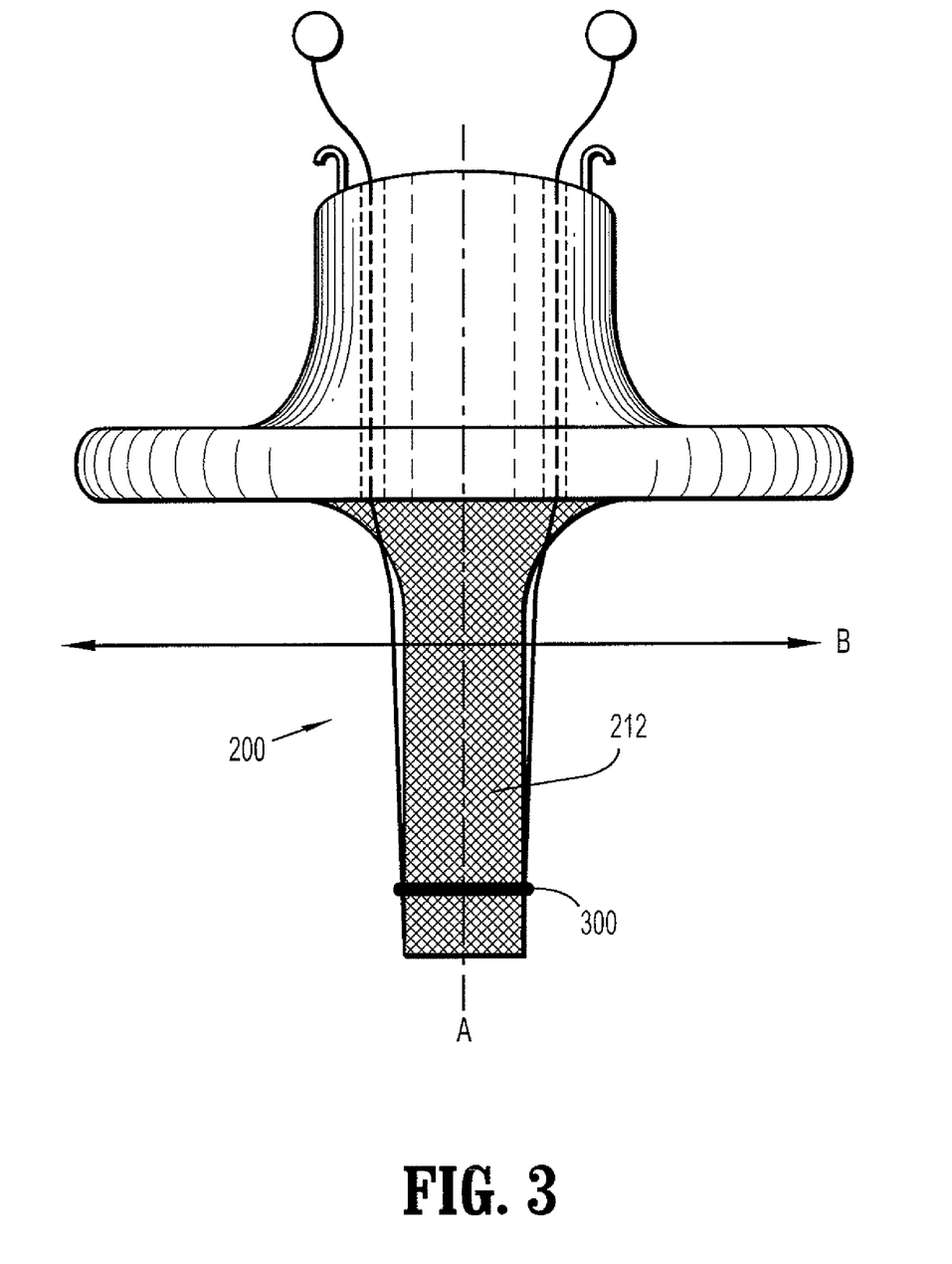
FIG. 3 is a side, schematic view of an alternative embodiment of the surgical access apparatus shown in FIG. 1.

The connective member 300 is secured to the tubular member 200, and may be positioned at any suitable location along the length "L" thereof. For example, the connective member 300 may be positioned adjacent the distal end 204 of the tubular member 200, as shown in FIGS. 1 and 2. The connective member 300 may positioned either within the lumen 210 (FIGS. 1 and 2), or alternatively, the connective member 300 may be positioned externally of the tubular member 200, i.e., the connective member 300 may be secured to an outer surface 212 of the tubular member 200 (FIG. 3).

Referring again to FIGS. 1 and 2, the surgical access apparatus 10 is illustrated as including a pair of filaments 400. In alternative embodiments of the present disclosure, however, the filaments 400 may be included in either greater or fewer numbers. The filaments 400 are secured to the connective member 300 such that the filaments 400 extend proximally therefrom, i.e., towards the housing 100, and may be secured to the connective member 300 in any suitable manner, such as through the use of adhesives or heat staking, for example. The filaments 400 are used to reposition the tubular member 200 from a first (initial) position (FIG. 1) to a second (activated) position (FIG. 2), and may be any members suitable for this intended purpose, including but not limited to surgical sutures, tape, etc.

In the first position, the tubular member 200 defines an initial outer dimension "$D_1$" that is substantially uniform along the length "L." The length "L" of the tubular member 200 in the first position may vary depending on the intended usage of the surgical access apparatus 10, but in general, will lie substantially within the range of about 10 cm to about 25 cm. However, a tubular member 200 that is substantially longer or shorter is not beyond the scope of the present disclosure. The initial outer dimension "$D_1$" of the tubular member 200 is smaller than the dimensions of the tissue tract 12 such that the tubular member 200 can be inserted and advanced distally through tissue tract 12 will little or no resistance when the tubular member is in the first position.

Upon the application of a force to the filaments 400 in the direction of arrow 1 (FIG. 1), e.g., by pulling or drawing the filaments 400 proximally, the tubular member 200 is shortened along the longitudinal axis "A", thereby transitioning into the second position (FIG. 2). In the second position, the tubular member 200 defines a length "$L_2$" that is considerably less than the initial length "L" defined by the tubular member 200 in the first position. Additionally, in the second position, the tubular member 200 defines a tissue engaging portion 214 having an outer dimension "$D_2$" that is considerably greater than the outer dimension "$D_1$" defined by the tubular member 200 in the first position. The tissue engaging portion 214 contacts the patient's tissue "T" about the tissue tract 12 and, in conjunction with the flange 110 of the housing 100, facilitates anchoring of the surgical access apparatus 10. It is envisioned that the tissue engaging portion 214 may also act to at least partially form a seal with the patient's tissue "T" to substantially reduce the likelihood that any fluids present within the surgical worksite "W," such as insufflation gasses or irrigant solutions, will escape around the surgical access apparatus 10.

With continued reference to FIGS. 1 and 2, the aforementioned manual members 500 are secured to the filaments 400, and are configured and dimensioned for engagement by the clinician to assist the clinician in transitioning the tubular member 200 from the first position (FIG. 1) to the second position (FIG. 2). Although illustrated as ring-shaped, it should be understood that the manual members 500 may be configured and dimensioned in any manner suitable for this intended purpose. Generally, the number of manual member 500 included as part of the surgical access apparatus 10 will correspond to the number of filaments 400. For example, as seen in FIGS. 1 and 2, the surgical access apparatus 10 includes a pair of filaments 400 connected to a pair of manual members 500. It is also envisioned, however, that each of the filaments 400 may be secured to the same manual member 500.

As previously indicated, the housing 100 of the surgical access apparatus 10 includes locking structure 600, which acts to maintain the tubular member 200 in the second position (FIG. 2). As seen in FIGS. 1 and 2, in one embodiment, the locking structure 600 includes one or more channels 602 that are formed in the housing 100, as well as one or more engagement members 604. The channels 602 extend at least partially through the housing 100 to one or more egresses 114 (FIG. 2) formed either in a proximal-most surface 116, as shown, or an outer wall 108 of the housing 100. In the illustrated embodiment, the filaments 400 extend through the channels 602 for grasping by the clinician, e.g., via the manual members 500, to thereby transition the tubular member 200 into the second position (FIG. 2). Upon repositioning of the tubular member 200 from the first position (FIG. 1) to the second position (FIG. 2), either or both of the filaments 400 and the manual members 500 are secured about the engagement members 604, e.g., by tying. The engagement members 604 may be any structure suitable for the intended purpose of releasably securing the filaments 400, such as the illustrated hook, for example.

Figure 4:
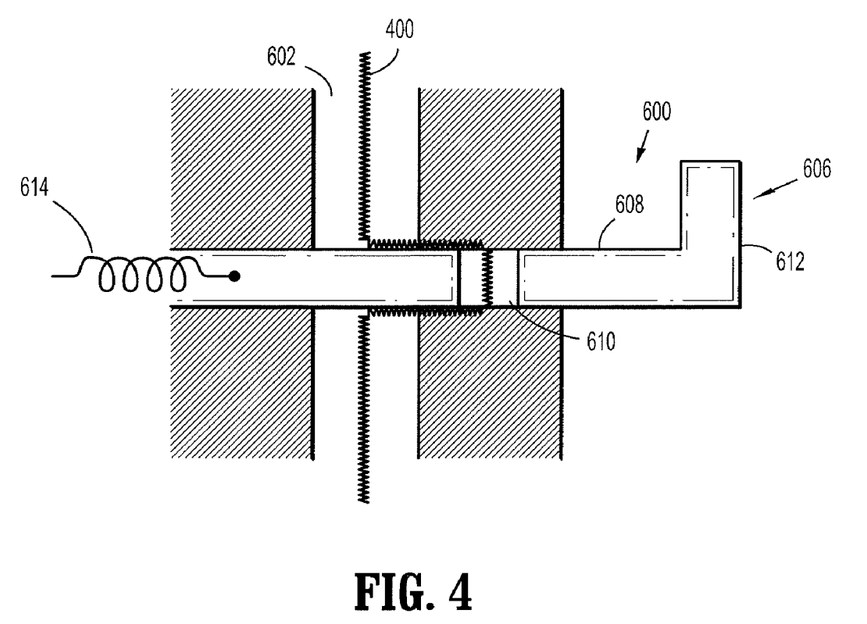
FIG. 4 is a side, cross-sectional view of one embodiment of locking structure for use with the surgical access apparatus shown in FIG. 1 illustrating the locking structure in a locked condition.
Figure 5:
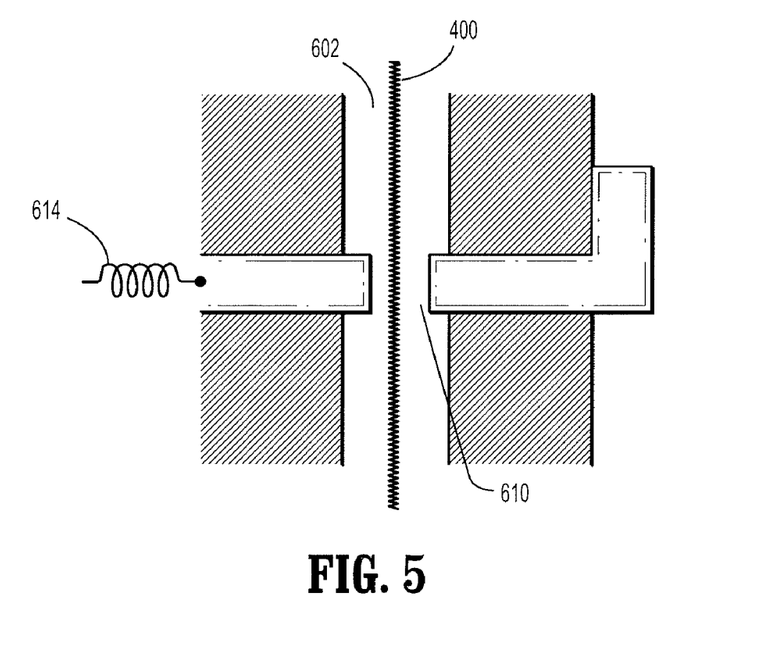
FIG. 5 is a side, cross-sectional view of the locking structure shown in FIG. 4 illustrating the locking structure in an open condition.

Referring now to FIGS. 4 and 5, in an alternative embodiment, the locking structure 600 includes the aforementioned channels 602 and a locking mechanism 606. The locking mechanism 606 includes a locking member 608 having an aperture 610 formed therein, a handle portion 612, and a biasing member 614. The aperture 610 is configured to receive the filaments 400, and the handle portion 612 is configured for manual engagement by the clinician to facilitate transitioning of the locking mechanism 606 between a locked condition (FIG. 4) and an open condition (FIG. 5). In the locked condition, the aperture 610 is in misalignment with the channel 602 such that a portion of the filaments 400 is disposed between the housing 100 and the locking member 608, effectively prohibiting any movement of the filaments 400 and thereby maintaining the second position of the tubular member 200 (FIG. 2). When the locking mechanism 606 is in the open condition, however, at least a portion of the aperture 610 is aligned with the channel 602 such that the filaments 400 may freely extend therethrough. The biasing member 614 urges the locking mechanism 606 towards the locked condition and may be comprised of any structure or mechanism suitable for this intended purpose, e.g., a spring.

In alternative embodiments, the locking mechanism 606 may comprise a single locking member 608 and a single biasing member 614, as shown in FIGS. 4 and 5, or a plurality of locking members 614 engagable with one or more biasing members 620.

Referring again to FIGS. 1 and 2, the use and function of the surgical access apparatus 10 will be discussed during the course of a typical minimally invasive procedure subsequent to the formation of the tissue tract 12.

Prior to insertion of the surgical access apparatus 10, the tubular member 200 is in the first position (FIG. 1) to facilitate positioning of the tubular member 200 within the tissue tract 12. It should be noted that the clinician may compress the connective member 300 radially, i.e., towards the longitudinal axis "A," to further reduce the outer transverse dimension "$D_1$" of the tubular member 200 at the distal end 204 to reduce the likelihood of trauma to the tissue "T" during insertion. After positioning the distal end 204 of the tubular member 200 within the tissue tract 12, the clinician advances the surgical access apparatus 10 distally until the flange 110 abuts the patient's tissue "T." Thereafter, the clinician draws the filaments 400 proximally towards the housing 100 to transition the tubular member 200 into the second position (FIG. 2) and form the tissue engaging portion 214. The clinician can then secure the filaments 400 to the locking structure 600 in order to maintain the second position of the elongated member 400, thereby anchoring the surgical access apparatus 10 within the tissue tract 12. The surgical instrument "I" can then be inserted into, and advanced distally through, the lumen 210 extending through the tubular member 200 to carry out the surgical procedure through the surgical access apparatus 10.

It should be noted that insertion of the surgical instrument "I" may expand the tubular member 200 outwardly along the transverse axis "B" into tight-fitting engagement with the patient's tissue "T," thereby further securing the surgical access apparatus 10 and enhancing the quality of the seal formed by the engagement of the tissue "T" with the flange 110 and the tissue engaging portion 214 of the tubular member 200.

After completing the procedure and withdrawing the surgical instrument "I" from the tubular member 200, the filaments 400 can be disengaged from the locking structure 600, e.g., untied, such that the tubular member 200 can be returned to the first position (FIG. 1). The surgical access apparatus 10 can then be withdrawn from the tissue tract 12, and the tissue tract 12 can be closed.

Figure 6:
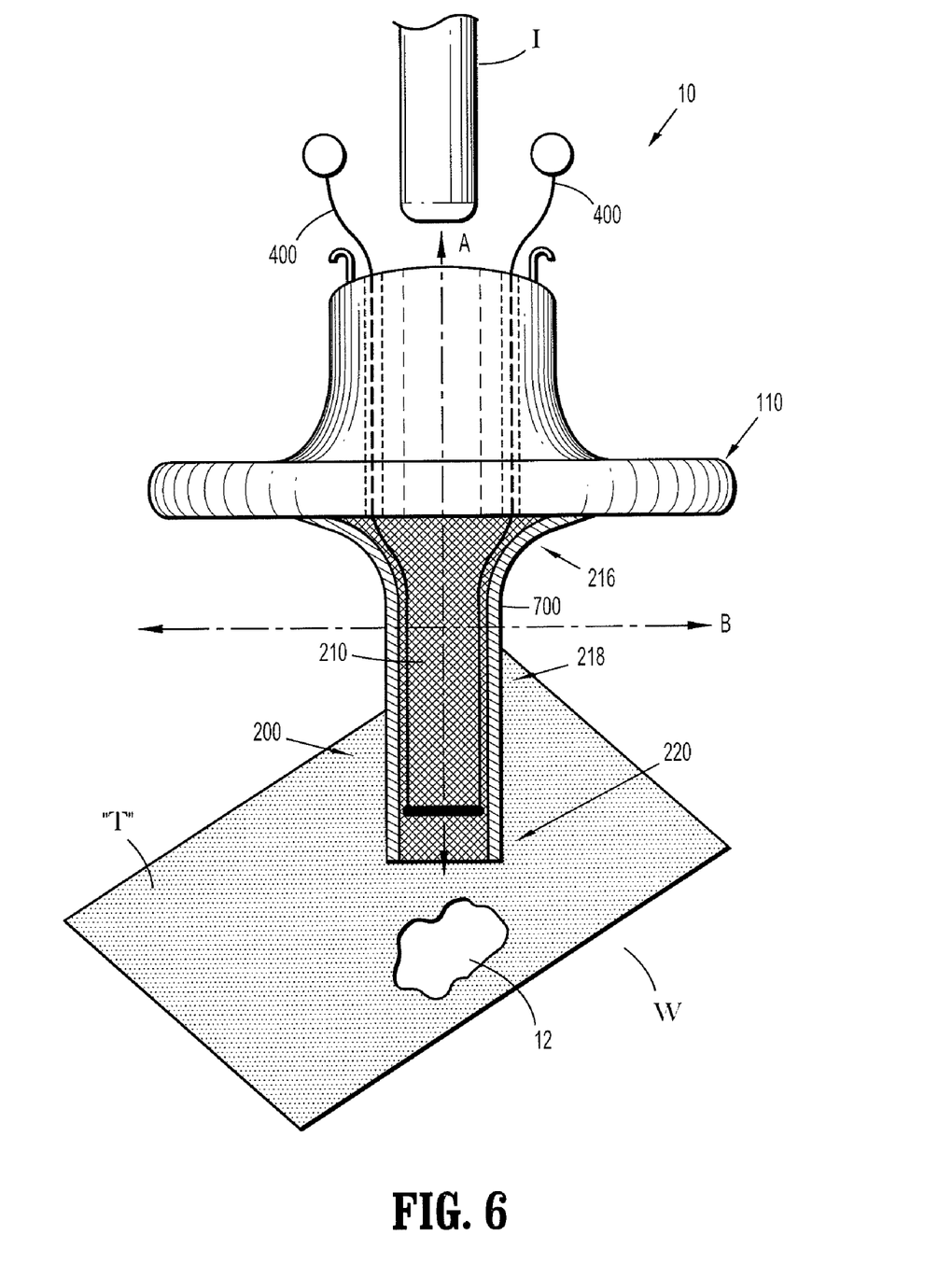
FIGS. 6 and 7 are side, schematic views of another embodiment of the surgical access apparatus shown in FIG. 1 including a membrane disposed about the tubular member, the tubular member being respectively shown in the first and second positions thereof.
Figure 7:
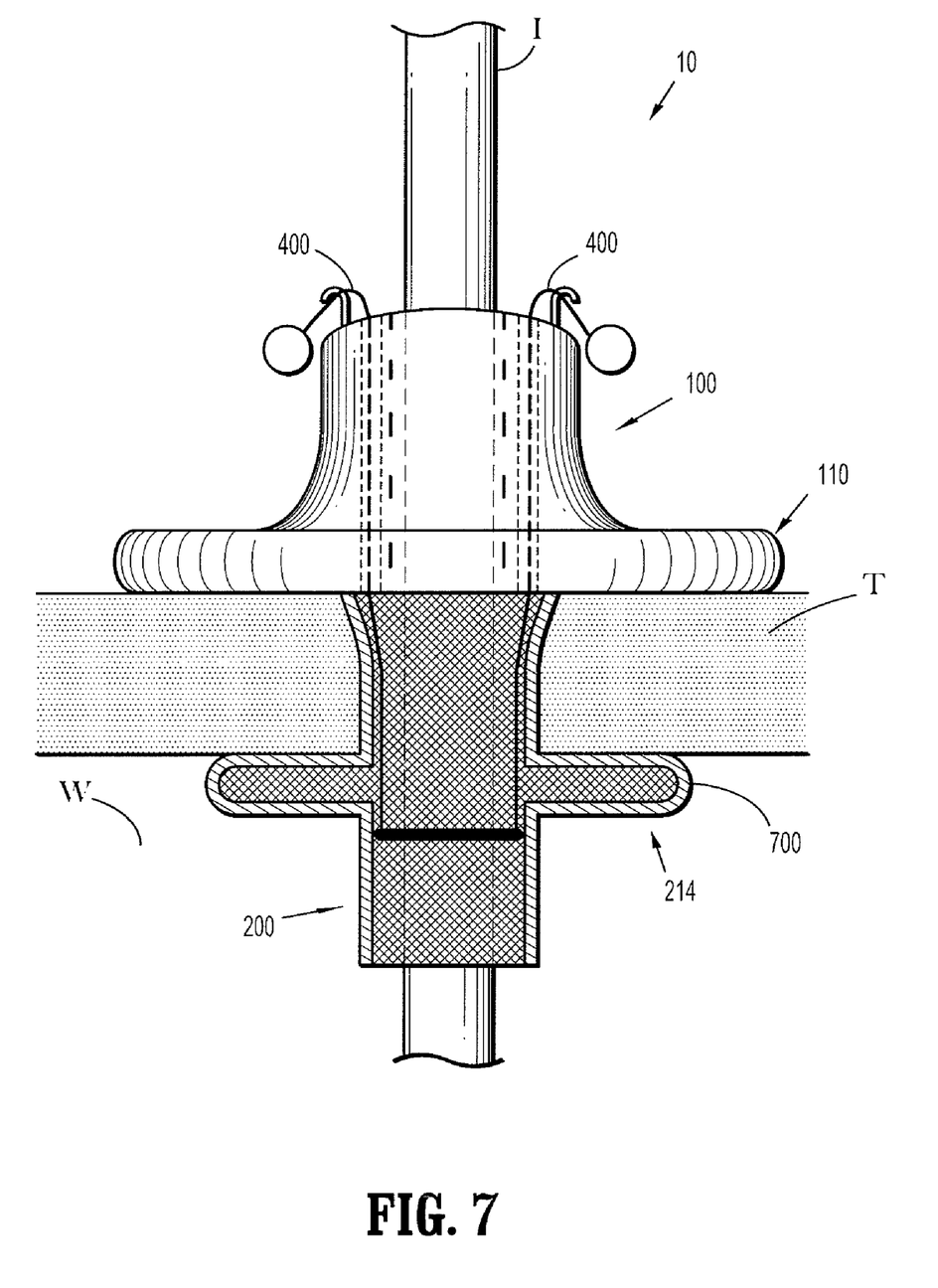

Referring now to FIGS. 6 and 7, in another embodiment, the surgical access apparatus 10 includes a membrane 700 that is disposed about the tubular member 200. The membrane 700 may be composed of any suitable biocompatible material that is at least semi-resilient in nature and substantially impervious to fluids, e.g., insufflation gas or an irrigant solution. Incorporating the membrane 700 may facilitate the insertion and passage of one or more surgical instruments "I" into and through the lumen 210 of the tubular member 200. The membrane 700 may be disposed about the tubular member 200 along its entire length, or in the alternative, the membrane 700 may be selectively disposed about individual sections of the tubular member 200, e.g., about a proximal section 216, an intermediate section 218, and/or a distal section 220.

When disposed about the proximal section 216 of the tubular member 200, the membrane 700 engages the patient's tissue "T" upon transitioning of the tubular member 200 from the first position (FIG. 6) into the second position (FIG. 7). Engagement of the membrane 700 with the patient's tissue "T," in conjunction with the flange 110 of the housing 100, creates a substantially fluid-tight seal about the tissue tract 12, thereby substantially inhibiting the escape of any fluids from the surgical worksite "W" about the surgical access apparatus 10.

As previously discussed with respect to the surgical access apparatus 10 shown in FIGS. 1 and 2, introducing the surgical instrument "I" to the tubular member 200 may cause the tubular member 200 to expand outwardly along the transverse axis "B." In the embodiment of the surgical access apparatus 10 seen in FIGS. 6 and 7, the membrane 700 would also be forced outwardly into engagement with the patient's tissue "T." Accordingly, the membrane 700 may act to further anchor the surgical access apparatus 10 within the tissue "T," and tighten the seal created therewith by the tissue engaging portion 214 and the flange 110.

The above description, disclosure, and figures should not be construed as limiting, but merely as exemplary of particular embodiments. It is to be understood, therefore, that the disclosure is not limited to the precise embodiments described, and that various other changes and modifications may be effected therein by one skilled in the art without departing from the scope or spirit of the disclosure. Additionally, persons skilled in the art will appreciate that the features illustrated or described in connection with one embodiment may be combined with those of another, and that such modifications and variations are also intended to be included within the scope of the present disclosure.

What is claimed is:

1. A surgical access apparatus for positioning within a percutaneous tissue tract to facilitate access to an underlying surgical worksite, the surgical access apparatus comprising:
    a housing having proximal and distal ends and being configured to removably receive at least one surgical instrument;
    a tubular member extending distally from the housing along a longitudinal axis, the tubular member defining an axial lumen configured and dimensioned to allow the at least one surgical instrument to pass therethrough, the tubular member being repositionable between a first position, in which the tubular member is configured for at least partial insertion into the tissue tract, and a second position, in which the tubular member is configured to facilitate anchoring of the tubular member within the tissue tract;
    a connective member secured to the tubular member, the connective member being configured to contact the at least one surgical instrument upon insertion to form substantially fluid-tight seal therewith; and
    at least one filament secured to the connective member and extending proximally therefrom, the at least one filament being movable in a longitudinal direction relative to the tubular member to cause corresponding movement of the connective member to thereby facilitate selective repositioning of the tubular member from the first position to the second position.

2. The surgical access apparatus of claim 1, wherein the tubular member includes a first outer dimension in the first position, the tubular member defining a tissue engaging portion in the second position with a second outer dimension larger than the first outer dimension.

3. The surgical access apparatus of claim 1, wherein the connective member is positioned within the lumen of the tubular member.

4. The surgical access apparatus of claim 1, wherein the connective member is secured to an outer surface of the tubular member.

5. The surgical access apparatus of claim 1, further including a membrane disposed about at least a portion of the tubular member to facilitate anchoring of the elongate member within the tissue tract.

6. The surgical access apparatus of claim 1, wherein the lumen of the tubular member includes an internal dimension smaller than an outer dimension of the at least one surgical instrument.

7. The surgical access apparatus of claim 6, wherein the tubular member includes a plurality of fibers braided together to define a mesh adapted for radial expansion to allow for insertion of the surgical instrument into the lumen of the tubular member.

8. The surgical portion assembly of claim 7, wherein the fibers include a substantially elastic material such that the tubular member maintains a substantially constant axial dimension upon radially expansion.

9. The surgical portion assembly of claim 7, wherein the fibers include a substantially inelastic material such that the tubular member experiences a measure of axial shortening upon radial expansion.

10. The surgical access apparatus of claim 1, including at least one manual member secured to the at least one filament, the at least one manual member being configured and dimensioned for grasping by a clinician.

11. The surgical access apparatus of claim 10, wherein the housing includes a locking structure configured to engage one or more of the at least one filament and the at least one manual member to thereby maintain the second position of the tubular member.

12. The surgical access apparatus of claim 11, wherein the locking structure includes at least one channel formed in the housing, the at least one channel being configured to at least partially receive the at least one filament.

13. The surgical access apparatus of claim 12, wherein the locking structure further includes a locking member repositionable between unlocked and locked positions, the locking member defining a channel therethrough configured to at least partially receive the at least one filament, the channel of the locking member and the channel formed in the housing being substantially aligned when the locking member is in the unlocked position.

14. The surgical access apparatus of claim 13, wherein the channel of the locking member and the channel formed in the housing are substantially misaligned when the locking member is in the locked position.

15. The surgical access apparatus of claim 14, wherein the locking member is biased towards the locked position by a biasing member.

* * * * *